United States Patent [19]

Van Heugten et al.

[11] Patent Number: 5,713,915
[45] Date of Patent: Feb. 3, 1998

[54] SURGICAL KNIFE BLADE

[75] Inventors: Anthony Van Heugten; John A. Bee, both of Tampa, Fla.

[73] Assignee: Rhein Medical, Inc., Tampa, Fla.

[21] Appl. No.: 751,118

[22] Filed: Nov. 15, 1996

[51] Int. Cl.$^6$ .................................................. A61B 17/32
[52] U.S. Cl. .................................... 606/167; 606/166
[58] Field of Search ................................. 606/166, 167, 606/107, 181, 169

[56] References Cited

U.S. PATENT DOCUMENTS

| | | | |
|---|---|---|---|
| 4,688,570 | 8/1987 | Kramer et al. | 128/305 |
| 5,098,438 | 3/1992 | Siepser | 606/107 |
| 5,201,747 | 4/1993 | Mastel | 606/167 |
| 5,203,865 | 4/1993 | Siepser | 606/166 |
| 5,217,476 | 6/1993 | Wishinsky | 606/167 |
| 5,222,967 | 6/1993 | Casebeer et al. | 606/166 |
| 5,224,950 | 7/1993 | Prywes | 606/166 |
| 5,336,235 | 8/1994 | Myers | 606/166 |
| 5,370,652 | 12/1994 | Kellan | 606/166 |
| 5,376,099 | 12/1994 | Ellis et al. | 606/166 |
| 5,405,355 | 4/1995 | Peyman et al. | 606/166 |

*Primary Examiner*—Michael Buiz
*Assistant Examiner*—Kevin Truong
*Attorney, Agent, or Firm*—David W. Pettis, Jr.

[57] ABSTRACT

A surgical knife blade of the type primarily intended for making incisions in the eye, though suitable for incising virtually any spherical surface, is disclosed. The blade is uniquely characterized by its construction to include cutting edge bevels of different transverse dimension on the anterior surface of the blade with respect to the transverse dimension of corresponding bevels on the posterior surface of the blade, such that the blade of this invention will incise a substantially straight, perpendicular cut into the eye or other spherical surface.

13 Claims, 5 Drawing Sheets

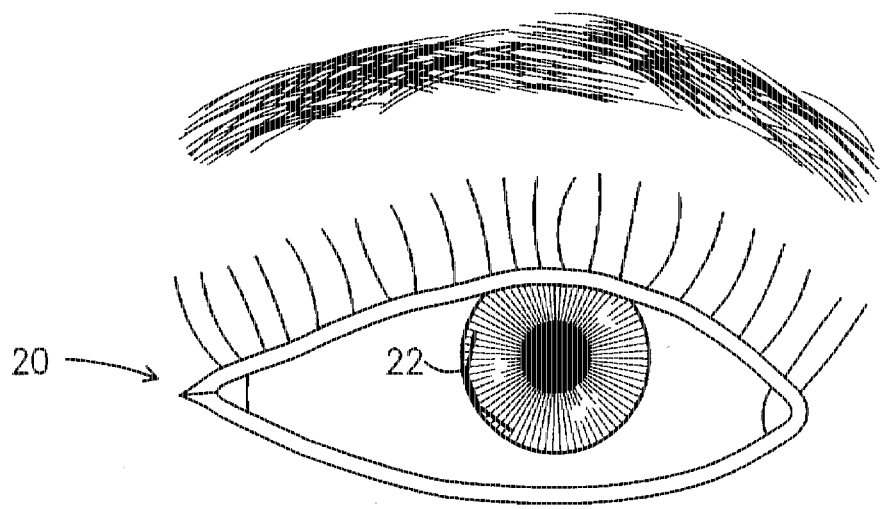
*Fig. 1*
PRIOR ART
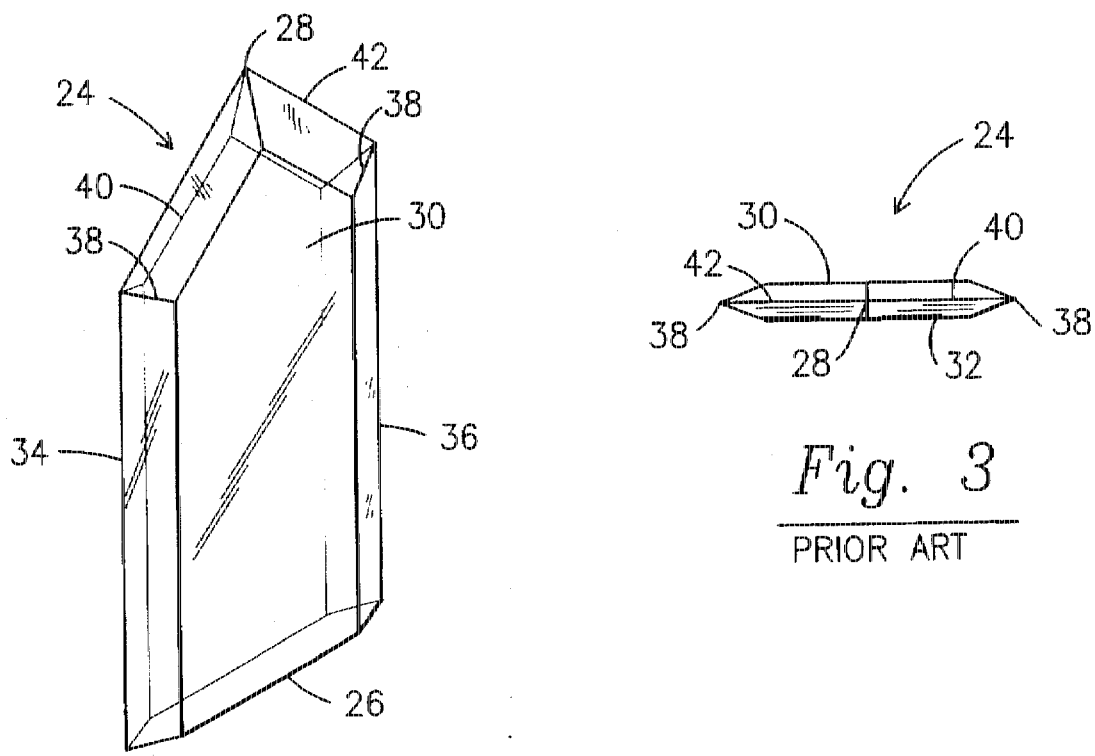
*Fig. 2*
PRIOR ART
*Fig. 3*
PRIOR ART

SURGICAL KNIFE BLADE

BACKGROUND OF THE INVENTION

1. Field of the Invention

The present invention relates to a surgical knife blade of the type primarily intended for making incisions in the eye, as for a clear corneal incision. The cutting edges of the blade are defined by the intersection of bevels formed on the blade's anterior surface and posterior surface, with the plane of the bevels with respect to the anterior and posterior surfaces being non-symmetrical.

2. Description of the Prior Art

Numerous prior art devices and blades are known for making incisions in the eye. Since the cornea and sclera are spherical, any blade penetrating their surface at an angle other than 90° will produce an irregular, or curved, incision line resembling a "smile." Ophthalmic surgeons have struggled with this problem for years, since curvilinear incisions are less likely to reapproximate as quickly, are less efficient, and are much less likely to create a suture-less water-tight seal. In an attempt to create substantially linear, perpendicular incisions, surgeons find themselves applanating the globe of the eye in an attempt to flatten it out, and invariably "dimple down" as soon as the tip of the blade reaches Descemet's membrane. However, problems are created with this "dimpling down" procedure in that it requires the surgeon to lift the back of the blade upwardly in order to point the tip of the blade downward. This maneuver causes the tissue in the corners of the external incision to tip, compromising its water-tight integrity and creating stromal distortion in the path of the tunnel. Lifting the back of the blade also increases the angle of the cut, making it less tangential to the circumferential arc of the cornea. This results in a reduced valve sealing surface area, further comprising water-tight integrity. In an attempt to compensate for this tearing of tissue, surgeons hydrate the corners of the incision. When a conventional flat blade enters a spherical object at an angle, as when making a clear corneal incision, it is the fact that the shoulders of the blade enter the globe closer to the center than the tip that produces the curved, "smile" incision.

While the phenomenon described above is certainly well-known and recognized when one attempts to incise the surface of a spherical member such as the eye, the producing of a curved incision derives most directly from the fact that state-of-the-art blades are typically symmetrical when the anterior surface is compared to the posterior surface. For example, U.S. Pat. No. 5,376,099 to Ellis, et at., discloses an undercut diamond surgical blade. However, when the bevels forming the cutting edges on the anterior surface of the blade are compared with the bevels on the posterior surface of the blade, one immediately recognizes that the bevels are identical. A similar construction is taught in U.S. Pat. No. 5,336,235 to Myers, even though the blade of that invention is slightly curved with respect to its major longitudinal axis.

The ophthalmologic surgical instrument disclosed in U.S. Pat. No. 4,688,570 to Kramer, et al., teaches the use of a cutting blade which is also quite symmetrical when the bevels of one surface of the blade are compared to the bevels on the other surface, those bevels defining the blade's cutting edge.

A variety of blade configurations are disclosed in U.S. Pat. No. 5,098,438 to Siepser, but the blades of that patent have bevels on only one of the blade surfaces.

While the blade disclosed in U.S. Pat. No. 5,201,747 to Mastel is shown as having three cutting edges, the bevels defining those cutting edges on the opposed surfaces of the blade are identical.

The blades disclosed in U.S. Pat. No. 5,203,865 to Siepser are virtually identical to those disclosed in the Siepser '438 patent.

A surgical blade similar to the Siepser blades in that bevels are provided on only one blade surface is taught in U.S. Pat. No. 5,370,652 to Kellan.

Finally, U.S. Pat. No. 5,217,476 to Wishinsky and U.S. Pat. No. 5,224,950 to Prywes each disclose surgical knife blades primarily for use in eye surgery wherein the cutting edges are defined by identical bevels on both surfaces of their respective blades.

It is, therefore, clear that there remains a great need in the art for a surgical knife blade capable of making a straight, linear incision to create a self-sealing clear corneal incision without having to "dimple down" into Descemet's membrane, with the increased risk of tearing tissue at the edges of the incision as is almost always encountered using the blades available today.

SUMMARY OF THE INVENTION

The present invention relates to a surgical knife blade of the type primarily intended for making incisions in the eye. While the blade may be formed from any suitable material such as, for example, precious or semi-precious stones and man-made equivalents thereof, steel, glass, or ceramics, the blade of this invention preferably comprises a diamond. The structure of the blade in a preferred embodiment comprises an elongated body having proximal and distal ends, anterior and posterior opposing surfaces, a shoulder intermediate the proximal and distal ends, first and second longitudinal sides between the proximal end and the shoulder, and first and second cutting edges between the shoulder and the distal end. The first and second cutting edges are formed by the intersection of first and second anterior bevels on the anterior surface with opposed first and second posterior bevels on the posterior surface. In this preferred embodiment the first and second anterior bevels are shorter at the distal end and longer at the shoulder. As used herein, the words "short" and "long" refer to the transverse dimension of the plane defined by the beveled surfaces with regard to the corresponding planar surface of the respective anterior and posterior surfaces. That is to say, the cutting edges formed by the intersection of the first and second anterior bevels with their corresponding first and second posterior bevels are closer to the plane of the anterior surface at the distal end and farther from that same plane at the shoulder.

The opposed first and second posterior bevels formed on the posterior surface are longer at the distal end, and shorter at the shoulder. Thus, as stated above, the cutting edges are farther from the plane of the posterior surface at the distal end and closer to that same plane at the shoulder.

The first and second longitudinal sides are formed by the intersection of third and fourth anterior bevels on the anterior surface with opposed third and fourth posterior bevels on the posterior surface. The third and fourth anterior bevels are substantially equal in length to the length of the first and second anterior bevels at the shoulder, and the third and fourth posterior bevels are substantially equal in length to that of the first and second posterior bevels at the shoulder. Thus, as is clearly illustrated and more fully described below, the third and fourth anterior bevels are relatively longer than the third and fourth posterior bevels.

In a first preferred embodiment, the first and second longitudinal sides of the blade of this invention are substantially parallel. In a second preferred embodiment, the first and second longitudinal edges diverge outwardly from the shoulder to the proximal end.

In this second preferred embodiment, the third and fourth anterior bevels become longer along a longitudinal axis from the shoulder to the proximal end, and the third and fourth posterior bevels become shorter along that same longitudinal axis.

The invention accordingly comprises an article of manufacture possessing the features, properties, and the relation of elements which will be exemplified in the articles hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 depicts an eye into which an incision has been made utilizing a typical prior art blade.

FIG. 2 is a perspective view of a typical prior art blade.

FIG. 3 is a distal end view of the typical prior art blade shown in FIG. 2.

Similar reference characters refer to similar parts throughout the several views of the drawings.

DETAILED DESCRIPTION OF THE PREFERRED EMBODIMENTS

Figure 4:
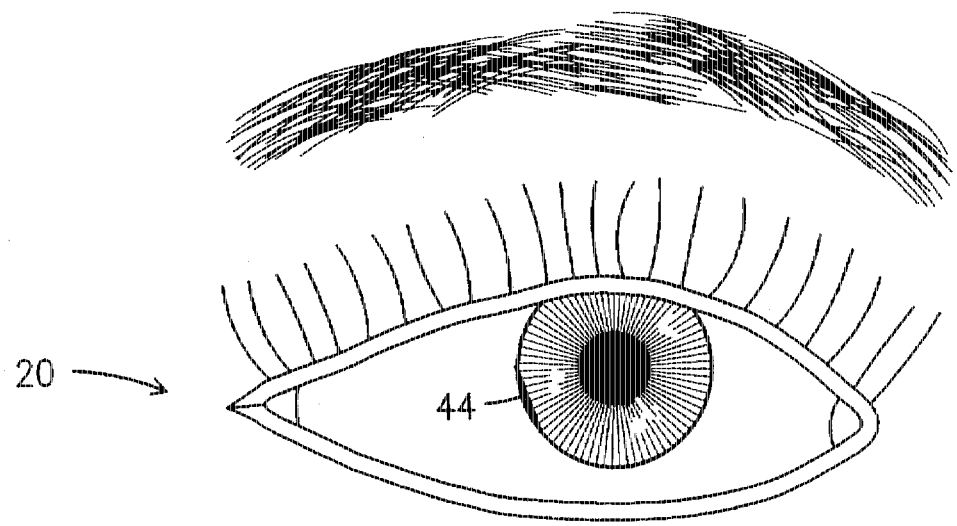
FIG. 4 depicts an eye with an incision made therein by the blade of this invention.

The views of FIGS. 1–3 illustrate the current state-of-the-art with regard to knife blades used for ophthalmic surgery. FIG. 1 illustrates an eye, generally indicated as 20, into which an incision 22 has been made utilizing a diamond blade such as that generally indicated as 24 in the views of FIGS. 2 and 3. As clearly seen in the view of FIG. 1, incision 22 is irregular and essentially "smile" shaped. Such an irregular incision 22 results from the geometry of the prior art blade 24. Referring to the views of FIGS. 2 and 3, blade 24 comprises an elongated body, preferably formed from a diamond, having a proximal end 26 and a distal end 28. Prior art blade 24 further comprises an anterior surface 30 and opposed posterior surface 32. First and second longitudinal sides 34 and 36 extend between proximal end 26 and shoulder 38 of blade 24. First and second cutting edges 40 extend from shoulder 38 to distal end 28.

As clearly seen in the view of FIG. 3, the intersection of anterior and posterior bevels defining first cutting edge 40 and second cutting edge 42 are substantially identical. Though not seen in the view of FIG. 3, the intersection of anterior and posterior bevels defining first longitudinal side 34 and second longitudinal side 36 are also substantially identical. That is to say, in prior art blade 24, the geometry of anterior surface 30, including its corresponding bevels, is substantially identical to the geometry of posterior surface 32 and its corresponding bevels. It is as a direct result of this symmetry of construction that a curved incision 22 results from the use of blade 24 to incise a spherical object such as the globe of eye 20.

Turning now to the remaining figures, FIG. 4 illustrates an eye 20 wherein a substantially linear, perpendicular incision 44 has been made. FIGS. 5–10 illustrate a first preferred embodiment of the surgical knife blade of this invention, generally indicated as 46. While blade 46 may be formed from any suitable material, the preferred material is diamond, and that is illustrated in the drawing figures.

Figure 5:
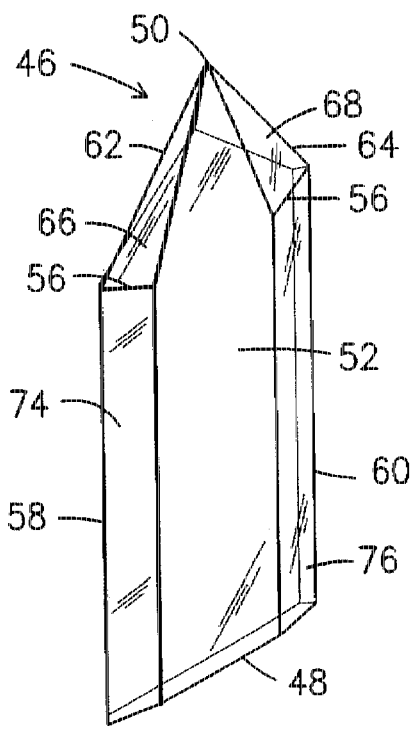
FIG. 5 is a perspective view of a first preferred embodiment of the blade of this invention.

With particular regard to the view of FIG. 5, it is seen that blade 46 comprises an elongated body having a proximal end 48 and a distal end 50. Referring to the view of FIG. 10, it can be seen that blade 46 further comprises an anterior surface 52 and an opposed, posterior surface 54. A shoulder 56 is intermediate proximal end 48 and distal end 50, and first and second longitudinal sides 58 and 60 extend from shoulder 56 to proximal end 48. First and second cutting edges 62 and 64 extend angularly from shoulder 56 to distal end 50.

The unique geometry of blade 46 provides for the substantially linear, perpendicular cut 44, as shown in the view of FIG. 4, without the necessity of the surgeon's applanating the globe to try to flatten it out, or "dimpling down" as soon as distal end 50 of blade 46 reaches Descemet's membrane. It is, in fact, the non-symmetrical planes of beveling with regard to anterior surface 52 as compared to the beveling on posterior surface 54 which results in the straight cut 44. These different planes actually guide the blade 46 to maintain a substantially linear, perpendicular incision 44 through the globe of eye 20 and Descemet's membrane.

Figure 6:
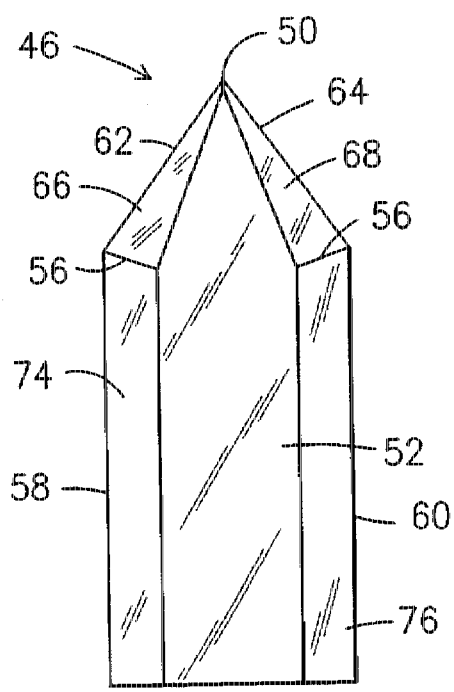
FIG. 6 is an anterior plan view of the blade shown in FIG. 5.

Referring to the planar view of FIG. 6, first and second cutting edges 62 and 64 are partially formed by corresponding first anterior bevel 66 and second anterior bevel 68. Also, as is clearly shown in the view of FIG. 6, the planes defined by first and second anterior bevels 66 and 68 are shorter adjacent distal end 50 and are longer adjacent shoulder 56, graduating therebetween in a substantially linear fashion.

Figure 7:
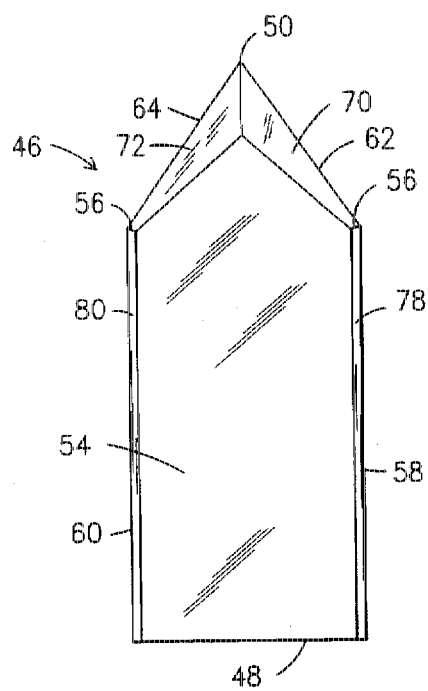
FIG. 7 is a posterior plan view of the blade shown in FIG. 5.
Figure 9:
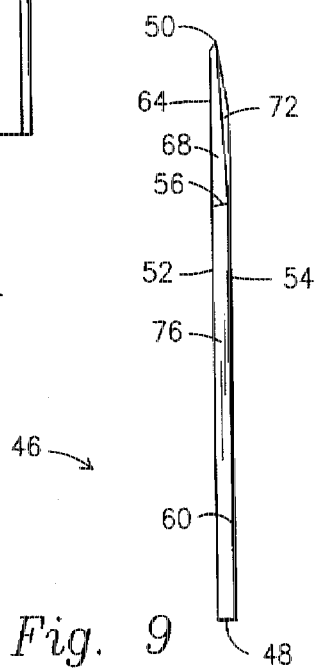
FIG. 9 is a left side view of the blade shown in FIG. 7.
Figure 8:
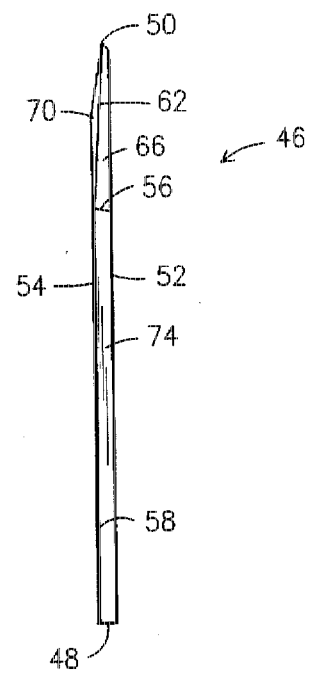
FIG. 8 is a right side view of the blade shown in FIG. 7.
Figure 10:
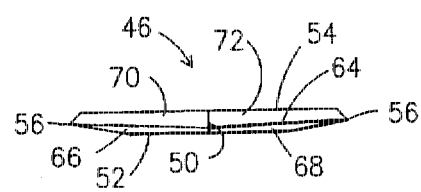
FIG. 10 is a plan view of the distal end of the blade shown in FIG. 7.
Figures 11, 12:
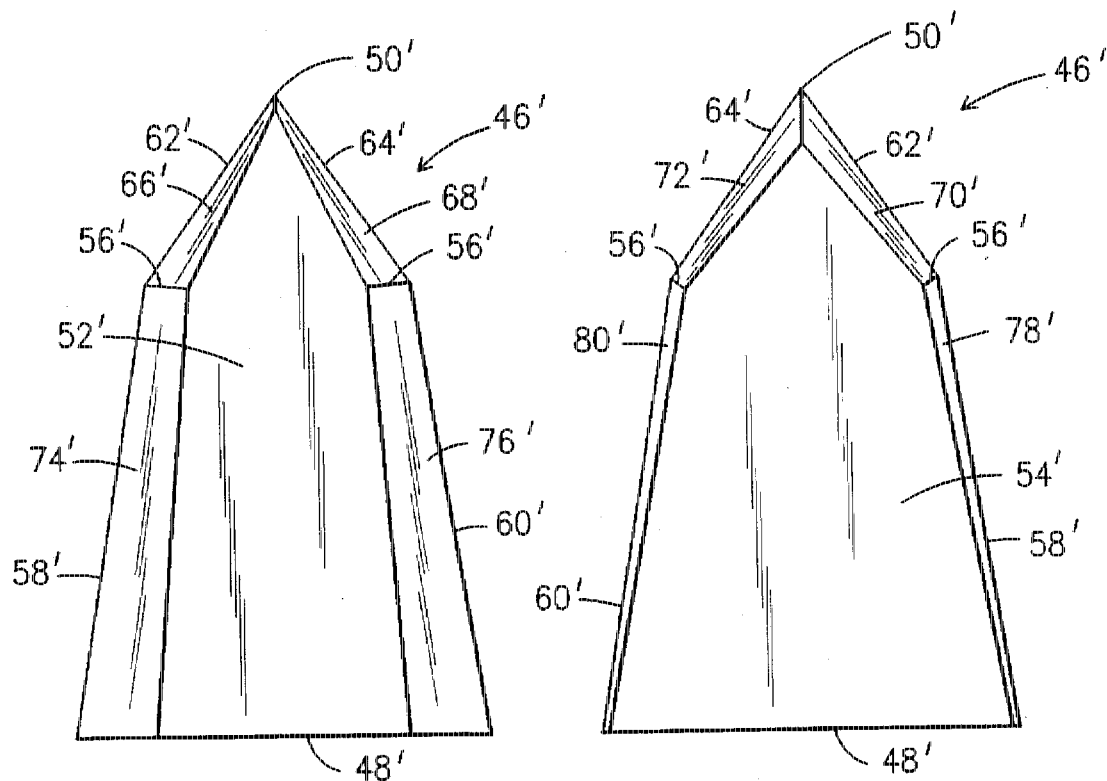
FIG. 11 is an anterior plan view of a second preferred embodiment of the blade of this invention.
FIG. 12 is a posterior plan view of the blade shown in FIG. 11.
Figure 13:
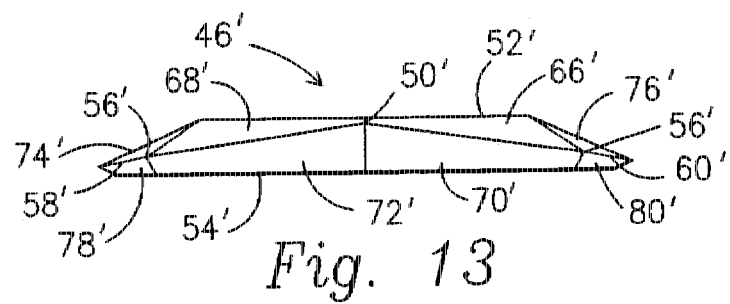
FIG. 13 is a plan view of the distal end of the blade shown in FIG. 11.
Figure 14:
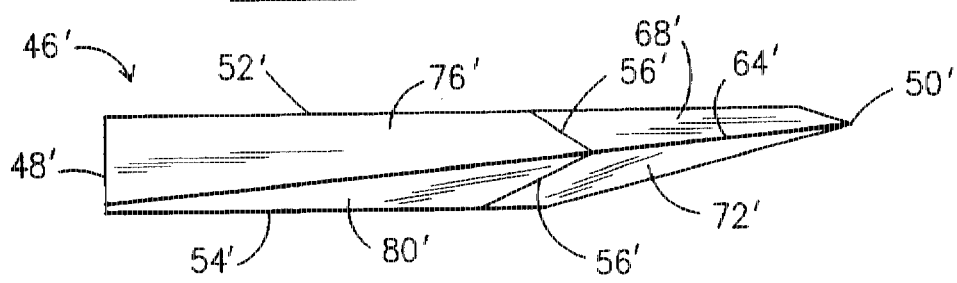
FIG. 14 is a right side view of the blade shown in FIG. 11.

Referring to the view of FIG. 7, corresponding, but opposed bevels are provided on posterior surface 54. First and second posterior bevels 70 and 72 partially define first and second cutting edges 62 and 64 from the posterior view of FIG. 7. As shown in the view of FIG. 7, the planes defined by first and second posterior bevels 70 and 72 are longer adjacent distal end 50, and are shorter adjacent shoulder 56.

Referring once again to the view of FIG. 6, first and second longitudinal sides 58 and 60 are partially formed, with respect to the anterior side of blade 46, by third and fourth anterior bevels 74 and 76, respectively. Looking at the posterior view of FIG. 7, first and second longitudinal sides 58 and 60 are partially formed by corresponding third and fourth posterior bevels 78 and 80, respectively.

As clearly shown in the views of FIGS. 6 and 7, the planes of third and fourth anterior bevels 74 and 76 are substantially equal to the length of first and second anterior bevels 66 and 68 at shoulder 56. In similar fashion, the length of third and fourth posterior bevels 78 and 80 are substantially equal to first and second posterior bevels 70 and 72 at shoulder 56. Finally, the length of third and fourth anterior bevels is, therefore, significantly greater than the length of third and fourth posterior bevels 78 and 80.

In this first preferred embodiment for blade 46, typical blade width, as measured between first and second longitudinal sides 58 and 60 generally falls in the ranges of about 2.5 mm to about 3.2 mm. The preferred thickness for blade 46, measured from anterior surface 52 to posterior surface 54, is about 0.2 mm. The preferred length of blade 46 from proximal end 48 to distal end 50 is about 6 mm. Shoulder 56 is formed about 1.75 mm below distal end 50.

Referring now to the views of FIGS. 11–14, those figures illustrate a second preferred embodiment for the blade of this invention, generally indicated as 46'. As is clearly evident from the views of FIGS. 11–14, the only structural differences between blade 46 and blade 46' is the construction of blade 46' to graduate to a wider transverse dimension from its shoulder 56' to its proximal end 48'. Accordingly, the structural elements of blade 46' are substantially identical to those of blade 46 and have been indicated in the drawings by the addition of a prime (') mark. The use of this second preferred embodiment of blade 46' is desirable as when the surgeon elects to utilize larger phacotips after the incision 44 has been initially made by first and second cutting edges 62' and 64'. In a blade 46', wherein the transverse distance between shoulders 56' is about 2.5 mm, the transverse width at proximal end 48' is preferably about 3.9 mm.

Figure 15:
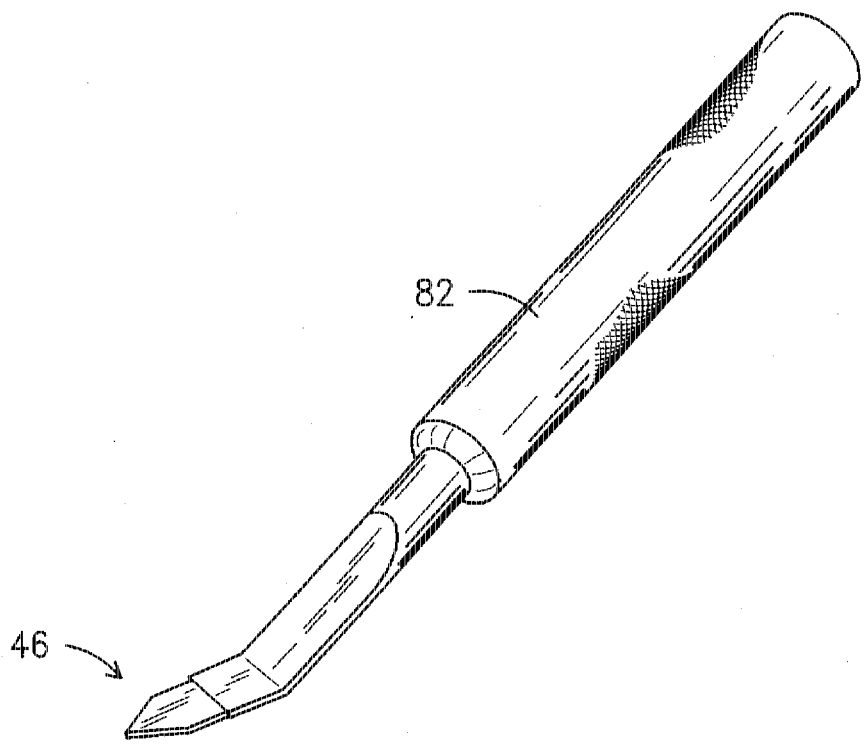
FIG. 15 depicts the first preferred embodiment of the blade of this invention operatively attached to an angled handle.
Figure 16:
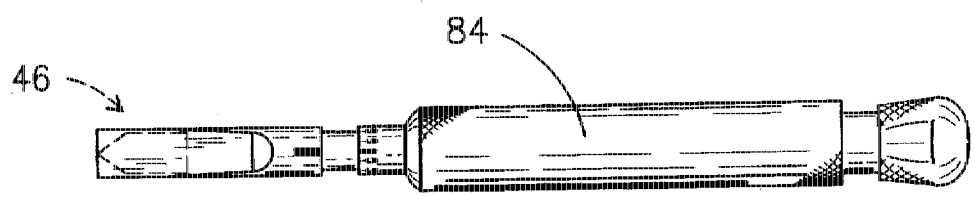
FIG. 16 depicts the first preferred embodiment of the blade of this invention attached to a step handle with the blade fully retracted.
Figure 17:
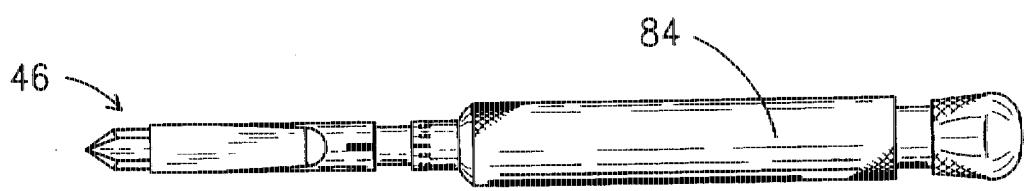
FIG. 17 is a view similar to that of FIG. 16 showing the blade fully extended.

Turning now to the views of FIGS. 15, 16 and 17, blade 46 is shown operatively attached to an angled handle in FIG. 15, and to a step handle 84 in the views of FIGS. 16 and 17. It is to be understood that the present invention is not to be limited to the use of any particular handle, but angled handle 82 and step handle 84 are equally well known and accepted for use in the field of ophthalmic surgery. Though not shown in the view of FIG. 15, the construction of angled handle 82 does permit full retraction of blade 46 in much the same fashion as is shown in the view of FIG. 16. Thus, it is the blade 46 or 46' and its unique construction as shown in the drawings and fully described above which permits a linear, perpendicular incision into the globe of the eye, and through Descemet's membrane, without the necessary of applanating the globe or "dimpling down" the knife blade which is the truly unique result of this invention.

It will thus be seen that the objects set forth above, among those made apparent from the preceding description, are efficiently attained, and, since certain changes may be made in the above product without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, What is claimed is:

1. A surgical knife blade of the type primarily intended for making incisions in the eye, said blade comprising: an elongated body having proximal and distal ends, anterior and posterior opposing surfaces, a shoulder intermediate said proximal and distal ends, first and second longitudinal sides between said proximal end and said shoulder, and first and second cutting edges between said shoulder and said distal end; said first and second cutting edges being formed by the intersection of first and second anterior bevels on said anterior surface with opposed first and second posterior bevels on said posterior surface, said intersection of said first and second anterior bevels with said first and second posterior bevels disposing said first and second cutting edges on a plane that is closer to the plane of said anterior surface than to the plane of said posterior surface at said distal end; and said first and second longitudinal sides being formed by the intersection of third and fourth anterior bevels on said anterior surface with opposed third and fourth posterior bevels on said posterior surface, said third and fourth anterior bevels being substantially equal to said first and second anterior bevels at said shoulder and said third and fourth posterior bevels being substantially equal to said first and second posterior bevels at said shoulder, said third and fourth anterior bevels each having a transverse dimension that is different from the corresponding transverse dimension of said third and fourth posterior bevels.

2. A blade as in claim 1 wherein said blade comprises a diamond.

3. A blade as in claim 1 wherein said first and second longitudinal sides are substantially parallel.

4. A blade as in claim 1 further comprising a handle attached to said proximal end.

5. A blade as in claim 1 wherein said shoulder comprises a width of about 2.5–3.2 mm.

6. A blade as in claim 1 wherein said intersection of said first and second anterior bevels with said first and second posterior bevels disposes said first and second cutting edges on a plane that is closer to the plane of said posterior surface than to the plane of said anterior surface at said shoulder.

7. A blade as in claim 6 wherein said first and second anterior bevels are about 0.1 mm in length at said distal end and about 0.5 mm in length at said shoulder.

8. A blade as in claim 7 wherein said first and second posterior bevels are about 0.8 mm in length at said distal end and about 0.1 mm in length at said shoulder.

9. A blade as in claim 6 wherein said third and fourth anterior bevels are about 0.5 mm in length.

10. A blade as in claim 9 wherein said third and fourth posterior bevels are about 0.1 mm in length.

11. A blade as in claim 1 wherein said first and second longitudinal edges diverge outwardly from said shoulder to said proximal end.

12. A blade as in claim 11 wherein said intersection of said third and fourth anterior bevels with said third and fourth posterior bevels disposes said first and second longitudinal sides on a plane that is closer to the plane of said posterior surface than to the plane of said anterior surface at said proximal end.

13. A blade as in claim 12 wherein said third and fourth anterior bevels are about 0.5 mm in length at said shoulder and are greater than about 0.5 mm at said proximal end and said third and fourth posterior bevels are about 0.1 mm in length at said shoulder and are less than about 0.1 mm at said proximal end.

* * * * *